United States Patent [19]

LaHaye et al.

[11] Patent Number: 5,075,116
[45] Date of Patent: Dec. 24, 1991

[54] COMPOSITION AND METHOD FOR TREATMENT OF MACULAR DEGENERATION

[75] Inventors: Peter G. LaHaye, Medina, Wash.; Randall J. Olson, Salt Lake City, Utah

[73] Assignee: LaHaye Laboratories, Inc., Medina, Wash.

[21] Appl. No.: 341,025

[22] Filed: Apr. 20, 1989

[51] Int. Cl.$^5$ .................... A61K 33/24; A61K 33/34; A61K 33/32; A61K 31/525; A61K 31/44; A61K 31/355; A61K 31/34; A61K 31/195

[52] U.S. Cl. .................................. 424/617; 424/630; 424/639; 424/641; 514/251; 514/345; 514/458; 514/474; 514/562; 514/912

[58] Field of Search ............... 514/474, 458, 912, 251, 514/345, 562; 424/630, 639, 641, 702, 617

[56] References Cited

U.S. PATENT DOCUMENTS 4,002,758  1/1977  Bigóu .................................. 514/912

OTHER PUBLICATIONS

Lawrence J. Machlin; "Free Radical Tissue Damage: Protective Role of Antioxidant Nutrients"; Clinical Nutrition, Hoffman–LaRoche Inc., Nutley, NJ 07110, U.S.A., FASEB 08926638/87/0001–0441; pp. 441–445.

*Primary Examiner*—Frederick E. Waddell
*Assistant Examiner*—Raymond J. Henley, III
*Attorney, Agent, or Firm*—Gordon W. Hueschen

[57] ABSTRACT

In accordance with the present invention, a composition is provided with Vitamins C and E, zinc, copper, selenium, manganese, and at least one of L-cysteine, pyridoxine, and riboflavin. The Vitamins C and E serve as antioxidants, while the zinc, copper, selenium and manganese serve as cofactors for metalloenzymes which scavenge oxidizers. The remaining three elements tend to enhance glutathione concentration. All the elements are provided in a tablet or caplet form which is suitable for oral ingestion. Preferably, the composition is taken periodically each day of a treatment period.

13 Claims, No Drawings

COMPOSITION AND METHOD FOR TREATMENT OF MACULAR DEGENERATION

BACKGROUND OF THE INVENTION

1. Field of the Invention

The present invention generally relates to methods and compositions to alleviate eye diseases and, more specifically, to improved methods and compositions for the treatment of cataracts and macular degeneration.

2. Description of the Related Art

Cataracts are a common problem throughout the world, with about one million cataract procedures performed annually in the United States alone. With an aging population, cataracts have become and will continue to become an increasing problem, resulting in a health care bill which could be measured in the billions of dollars. Macular degeneration associated with aging and drusen is another extremely significant concern, and is now a major cause of blindness in the United States for individuals over 65 years of age. Just at the period of time when the eyes are a most important sense, and reading and watching television are often the most enjoyable avenues of entertainment, this disease robs the elderly patient of this possibility.

The crystalline lens of the eye has only one disease state that we are aware of, and that is cataract. The lens loses its clarity as it becomes opacified, and vision is disturbed depending on the degree of opacification. There are different etiologies for cataracts such as a congenital lesion or trauma, which are well recognized. It is also known that some medicines such as cortisone-type preparations and glaucoma medications can cause cataracts, as can inborn metabolic errors such as galactosemia. These, however, are relatively uncommon in comparison to the common aging cataract, which shows an increase in frequency directly correlated with age.

The exact incidence of cataracts in the general population is difficult to determine because it depends on one's definition of a cataract. If defined as simply a lens opacity, then obviously the incidence is much higher than when defined as a lens opacity that significantly impacts vision. The pathogenesis of age-related cataracts or macular degeneration is incompletely understood. This common problem of cataracts is generally gradually progressive, except for the type which looks like crystals on the back surface of the lens and posterior subcapsule, which can often be rapidly progressive. The important point about cataracts, however, is that they do not spontaneously improve and the only effective treatment to date is surgery at a high cost.

Macular degeneration associated with aging and drusen also appears to be a biodegeneration with no effective treatment to date except with laser treatment in patients who develop abnormal vessels under the retina, i.e., subretinal neovascularization. The treatable group is a distinct minority of a much larger group. That means that individuals so afflicted can anticipate either a progressive deterioration or at times a relatively static course, but no spontaneous improvement, since the basic architecture of the retina is destroyed. Occasionally, there may be variations in vision which seem to show improvement depending on such things as lighting in the room and potential resolution of fluid underneath the retina. The important point, however, is that when this sensitive neurologic tissue is damaged, that damage is permanent.

As to cataracts, one common hypothesis to explain cataract development is premised on changes in the structure of the soluble lens proteins. Spector, Science 204:1323, 1979. (That article, as well as the following referenced articles and patents, are incorporated herein by reference.) This hypothesis suggests that soluble proteins form macromolecules greater than $50 \times 10^6$ daltons and large water-insoluble components. These aggregates, according to this hypothesis, act as scatterpoints of light and cause loss of lens transparency. It has been suggested that high molecular weight aggregates are precursors to the water-insoluble fraction. In cataractous lenses, a large disulfide-linked component has been found in the water-insoluble fraction. This is apparently not found in normal lenses. Spector, Proc. Natl. Acad. Sci. 75:3244, 1978.

As early as 1980, Spector et al. believed that the evidence supported the hypothesis that extensive oxidation of lens proteins occurs with cataracts, and that it begins at the fiber membrane. Spector, Proc. Natl. Acad. Sci. 77:1274, 1980. Specifically, Spector et al. indicated that many of the lens changes with cataracts may be caused by oxidative post-translational modification.

One major modification involves the oxidation of the thiol group of cysteine. They also note that the number of disulfide bonds increases with the severity of the cataract. Further, a concomitant conversion of methionine to methionine sulfoxide occurs in senile cataract, and they furthermore note that the oxidation products of tryptophan and tyrosine contribute to the abnormal fluorescence and color of the lens.

Spector et al. concluded in 1980 that oxidation of the sulfur-containing amino acids appears to first occur primarily at the membrane, then to the extrinsic membrane, and finally to the cytoplasmic proteins. However, Spector et al. could not conclude that oxidation of membrane sulfur was necessary for cataract formation.

At that time, Spector et al. indicated the uncertainty of the mechanism leading to oxidative damage. Yet, they noted that transient oxidative molecules, such as hydrogen peroxide and superoxide, are formed in the electron transport chain, in addition to other enzyme systems. (See also Spector, Exp. Eye. Res., 33:673, 1981.) They indicated the belief that the enzymes catalase, superoxide dismutase (SOD), and glutathione peroxidase (GSHPx) convert the transient molecules to innocuous compounds. In the cataractous lens, they surmised, the enzymes might be inactive.

Also in 1980, Garner et al. believed that cysteine and methionine oxidation did occur in clear regions of the lens. However, higher sulfur oxidation states, disulfide-linked high molecular weight aggregates, and cytoplasmic polypeptides disulfide-linked to membrane are only in the opaque regions. Garner, Exp. Eye Res., 31:361, 1980. The latter occurrence would result from low glutathione and thereby an inoperativeness of GSHPx and potential loss of catalase, which would allow free and abnormally high levels of $H_2O_2$ to react nonspecifically with venticular proteins. Spector, Exp. Eye Res., 33:673, 1981.

In 1981, Spector et al. stated that, notwithstanding the above observations, there still remained questions concerning the mechanism and agents involved with massive oxidation of the lens tissue and its relationship to cataract development. Spector, Exp. Eye Res., 33:673, 1981. They also noted that glutathione (GSH) can act as a reducing agent and free radical trapper. GSHPx and catalase are present to metabolize $H_2O_2$. SOD can detoxify $O_2$, and light can photochemically induce oxidation. However, Spector et al. believed that the actual roles of light and/or metabolically-generated oxidized components are unclear as to causing the observed oxidation products.

In 1987, Machlin et al. reported that there was some evidence that free radical damage contributed to the etiology of some diseases, including cataract. FASEB J. 1:441-45, 1987. They indicated that defenses against such free radical damage included Vitamin E, Vitamin C, betacarotene, zinc, iron, copper, manganese, and selenium.

As recently as 1988, in an article by Jacques et al., "Antioxidant Status in Persons With and Without Senile Cataract," Arch. Ophthal. 106:337, 1988, it is reiterated that it is commonly believed that oxidative mechanisms are causally linked to, not simply associated with, cataract formation. According to Jacques et al., the evidence suggests that GSHPx and SOD decrease with increasing degree of cataract. They further believe that the evidence indicates that low glucose-6-phosphate dehydrogenase (G6PD) activity is associated with increased risk of cataract. Low G6PD activity, as interpreted by Jacques et al., may lower the supply of reduced nicotinamide-adenine dinucleotide phosphate needed for protection of reduced glutathione, with reduced nicotinamide-adenine dinucleotide phosphate being a cofactor for the enzyme glutathione reductase.

Jacques et al. further reported that Vitamin E is believed to be a determinant of cataract formation and can act synergistically with GSHPx to prevent oxidative damage. They point out the possibility that Vitamin C may have a role in cataract formation and might influence GSHPx through its ability to regenerate Vitamin E. Betacarotene is indicated as a known antioxidant and could have a potential role in lens protection. Based on their studies, Jacques et al. concluded that antioxidant status had a potential role in cataract formation.

However, they pointed out that their study indicated that there was little evidence to suggest any relationship between erythrocyte enzyme levels and cataract occurrence. According to Jacques et al., the vitamins and combined indexes (SOD, GSHPx, and G6PD) appear to be only antioxidant markers associated with cataract risk. The relationship between the combined indexes and cataract occurrence is not explained.

If a treatment modality could slow down the progression of cataracts or macular degeneration, it would have a tremendous impact on the number of individuals who suffer from these problems due to the fact that they both occur toward the end of life. Toxicity from free radicals and oxidizers has generated significant interest in both diseases. There is circumstantial evidence at present to indicate that protection against phototoxicity and oxidizers could slow the onset and progression of both problems.

While the problems associated with cataracts and macular degeneration have long been recognized, and many attempts have been made to identify the causative factors and to solve such problems, those diseases still remain as major health problems.

A need therefore still exists in the art to provide improved methods and compositions for the treatment of cataracts and macular degeneration in the absence of surgery.

SUMMARY OF THE INVENTION

Accordingly, an object of the present invention is to provide a treatment methodology for eye diseases.

Another object of the present invention is to provide a safe yet effective composition for the treatment of cataracts and macular degeneration.

Still another object of the present invention is to provide a composition for scavenging free radicals and other oxidants associated with eye diseases.

In accordance with the present invention, a composition is provided with Vitamins C and E, zinc, copper, selenium, manganese, and at least one of L-cysteine, pyridoxine, and riboflavin. The Vitamins C and E serve as antioxidants, while the zinc, copper, selenium and manganese serve as cofactors for metalloenzymes which scavenge oxidizers. The remaining three elements tend t glutathione concentration. All the elements are preferably provided in a caplet form which is suitable for oral ingestion. Preferably, the composition is taken periodically each day of a treatment period.

The above and additional objects of the present invention can best be seen from an examination of the following specification and claims.

DETAILED DESCRIPTION OF THE PREFERRED EMBODIMENTS

The following description is provided to enable any person skilled in the art to which the present invention pertains, or with which it is most nearly connected, to make and use the same, and sets forth the best mode contemplated by the inventors of carrying out their invention.

According to the present invention, the elements of the composition are directed to scavenge free radicals and oxidants or in other ways retard disease progression of at least cataracts and macular degeneration. The free radicals to which the present invention is directed primarily include superoxide. The oxidants primarily include peroxide.

The items and doses in the present invention are consistent with those readily available in health food stores. The composition is preferably in tablet or caplet form for oral administration, with the patient taking four tablets or caplets twice a day. The present invention, however, contemplates that the preferred total dosage can be administered as a single dose or other multiple part dosages. Of course, other known avenues of administration can be employed, such as an absorbent patch that is adhered to a patient. The composition may also be of the timed release type. Further, for oral administration, the present composition may be in capsules, lacquered tablets, or unlacquered tablets, according to well-known methods. In accordance with the preferred multiple dosages described above, each tablet or caplet is preferably composed as follows:

Vitamin C

It has been known that there are high concentrations of Vitamin C both in the normal human lens and in the aqueous humor that surrounds the lens, and that this is an antioxidant. Harris, Nature 132:27-8, 1933. It has also been shown in the past that generally increasing dietary Vitamin C generally increases the concentration of ascorbate in the aqueous humor and in the human lens. Ringvold, Acta, Ophthalmologica 63:227-80, 1985. It has also been known that Vitamin C concentrations decrease with age and, in particular, in patients who have senile cataract. Chatterjee, Arch, Ophthalmol 56:756-60, 1956; Purcell, Arch, Ophthalmol 51:1-6, 1954; Consul, Eye, Ear, Nose and Throat Monthly 47:77, 1968. However, the latter study concluded that a fall in the level of ascorbic acid is not related to the causation of cataract. Purcell, supra. concluded that the therapeutic administration of Vitamin C to patients with cataracts appears irrational.

There is no known optimal daily dose of Vitamin C, although the U.S. RDA is 60 mg. However, dosages of 2.0 grams and more have frequently been taken as a supplement for general health. Although ascorbic acid or rose hips can be used, the present composition preferably utilizes Vitamin C in the form of sodium ascorbate because of it being easily dissolved in the digestive system and causing relatively minimal irritation. The concentration is at about 250 mg/tablet or caplet, or a total dosage of 2 grams/day. In such concentrations, the Vitamin C represents about 29.675% by weight of each tablet or caplet, which includes active as well as inactive ingredients described below.

Vitamin E

Vitamin E is also a well-known antioxidant, as already mentioned. See also Mansour, Invest. Opthal. Vis. Sci. (Supp) 25:138, 1984. As also mentioned above, Vitamin E can work synergistically with Vitamin C in protecting vital cell function from normal oxidants. Orten: *Human Biochemistry* 10th Edition, CV Mosby Co., 1982, p. 756.

A very common Vitamin E supplementation consists of 400 units per day. While one study which used 800 units per day showed questionable signs of toxicity, many common dietary supplements available in supermarkets have 1000 units of Vitamin E daily. Chaney: *Textbook of Biochemistry with Clinical Correlations.* John Wiley & Sons, 1986, pp. 970-1. The U.S. RDA is 300 units. The present invention preferably uses Vitamin E in the form of d-alpha tocopherol because of the ease of dissolving and minimal irritation. The concentration is at about 75 units/tablet or caplet or a total daily dosage of 600 units of Vitamin E. This represents about 8.484% by weight of each tablet or caplet.

Zinc

Zinc is known to be important to the health of the retina and the function of Vitamin A. Russel, Ann Int Med 99:227-39, 1983; Karcioglu, Surv Ophthalmol 27:114-22, 1982; Leure-duPree, Retina 2:294-302, 1982; Leure-duPree, Invest Ophthalmol Vis Sci 23:425-34, 1982. Zinc is one supplement previously used in a study which showed it to be significantly better than placebo in retarding macular degeneration changes. Newsome, Arch Ophthalmol 106:192-8, 1988. Zinc is also known to be an important cofactor for a whole multitude of metalloenzymes, not the least of which is superoxide dismutase, which scavenges the potent oxidizer - superoxide, as described above. There are two types of SOD in mammalian cells. One type contains copper and zinc and is located in the cytosol and periplasmic space of the mitochondria. The other type contains manganese and is in the matrix of the mitochondria (see generally U.S. Pat. No. 4,657,928). This is of particular import because both superoxide dismutase activity and zinc are dramatically lower in cataract patients than in noncataract patients. Ohrloff, Graefe's Arch Clin Exp Ophthalmol 222:79-81, 1984; Varma, Ophthalmic Res 9:421-31, 1977; Swanson, Biochem Biophy Res Comm 45:1488-96, 1971.

About 200 mg of zinc per day, although well-tolerated, has been shown to have potential side effects, particularly blocking copper absorption, which results in the possibility of copper deficiency anemia. Fischer, J Nutrition 113:462-9, 1983. High doses have also been shown to have the effect of lowering high density lipoprotein which may exacerbate atheroscterosis. Hooper, JAMA 244:1960-1, 1980.

The dosages of 100 mg of zinc a day and 150 mg of zinc a day have been known in the past to be well tolerated without difficulty. Wagner, Geriatrics 40:111-25, 1985. The U.S. RDA is 15 mg. While other salt forms such as sulfates and phosphates can be used, the present invention preferably provides the zinc, as with the other cofactors, in the form of zinc gluconate because of it being easily dissolved and causing minimal irritation. The concentration is at about 12.5 mg of zinc in each tablet or caplet for a total dosage of approximately 100 mg/day. Zinc gluconate represents about 1.414% by weight of each tablet or caplet.

Copper

Copper is another important cofactor for metalloenzymes, and is a second necessary cofactor for superoxide dismutase. Beem, J Biol Chem 249:7298, 1974. Copper has been shown to decrease in individuals over 70 years of age and to be basically zero in cataractous lenses. Swanson, Biochem Biophy Res Comm 45:1488-96, 1971. If copper is significantly decreased, superoxide dismutase has been shown to have decreased function, thereby hampering an important protective lens mechanism. Williams, Pediat Res 11:823, 1977. Copper is also protective of zinc toxicity, which blocks some of the zinc absorption and, therefore, decreases bioavailability. Van Campen, J Nutrition 97:104-8, 1970.

2-3 mg of copper per day has been estimated to be safe and provide adequate daily dietary intake. Pennington, J Am Dietetic Assoc 86:876-91, 1986. 2 mg is the U.S. RDA. Some copper absorption will be blocked by the 100 mg of daily zinc as provided above. Van Campen, J Nutrition 97:104-8, 1970. Therefore, the present composition utilizes about 0.5 mg/tablet or caplet, or a total of 4 mg/day. This amount is believed safe because in the typical American diet, particularly among the elderly, zinc and copper are often significantly below minimum daily requirements. In this embodiment of the present invention, copper is provided in the form of copper gluconate and copper gluconate represents about 0.058% by weight of each tablet or caplet.

Selenium

Selenium is another metal which has been known to be markedly deficient in cataracts versus clear lenses Swanson, Biochem Biophy Res Comm 45:1488-96, 1971. Selenium is a necessary cofactor for metalloenzymes, particularly GSHPx, which scavenges peroxides. Chaney, at p. 988. A past study showed macular degeneration being inversely related with plasma activity of GSHPx and suggested that its activity is an indication of the adequacy of selenium nutritional status. Weiter, Invest Ophthalmol (Supp) 26:58, 1985. Other studies have documented that selenium deficiency results in markedly decreased activity of lens GSHPx in animals, and the addition of selenium in selenium deficient animals blocked cataract formation. Whanger, Nutr Rep Int 12:343, 1975; Lawrence, Exp Eye Res 18:563, 1974.

The presently-accepted safe and adequate daily dietary intake of selenium is about 50 to 200 micrograms (mcg) for an adult. There is no U.S. RDA for selenium. Typical dietary intake for adults is in the lower end of the above range. A presently accepted, estimated maximum safe daily selenium human intake is 5 micrograms per kilogram of body weight per day. In the present composition, selenium is added at about 12.5 mcg/tablet or caplet, or a total of 100 mcg/day. Selenium, which is preferably bound with a primary dried yeast, represents about 1.13% by weight of each tablet or caplet.

Manganese

In general, manganese concentration has been known to decrease in cataracts versus clear lenses, although not nearly as dramatically as copper, zinc and selenium. Swanson, Biochem Biophy Res Comm 45:1488-96, 1971. Manganese is an important cofactor for metalloenzymes Orten, at pp. 725-6. As briefly noted above, a second type of superoxide dismutase exists in the mitochondria and has manganese as a necessary cofactor. Another metalloenzyme, to which manganese is a cofactor, is methionine adenosyltransferase, which is found in the lens. See generally Geller, Exp. Eye. Res. 43:998, 1986.

There is no presently known minimum daily requirement of manganese. However, a daily dose of 10 mg is an accepted safe amount and commonly available in the supermarket. Preferably, manganese is provided in the present composition at about 1.25 mg/tablet or caplet, or a total of 10 mg/day. This represents about 0.145% by weight, while preferably being provided in the form of manganese gluconate.

L-Cysteine

Glutathione (GSH), a tripeptide which includes L-cysteine, has been called the Achilles' heel of the human lens system. Cole, JAMA 254:1008, 1985. It, as alluded to above, acts directly as an antioxidant intracellularly and is also an important constituent of many enzymes, not the least of which is GSHPx, which reduces the potent oxidizer - peroxide. Reddy, Exp Eye Res 11:310-28, 1971; Bhuyan, Biochem Biophys Acta 497:641-51, 1977; Kinoshita, Am J Ophthalmol 46:36-41, 1958; Pirie, Biochem J 96:244-53, 1965. Glutathione has been known to decrease in concentration in human cataracts. Consul, Eye, Ear, Nose and Throat Monthly 47:77-80, 1968. Of the three constituent amino acids, L-cysteine is the one which has been thought to be rate limiting in regard to glutathione synthesis. Rathbun, In: Hockwin 0 (Ed.) Altern der Linse, Wilhelm Mayr, 1982, pp. 169-74.

L-cysteine is a naturally occurring amino acid. A total dose of 400 mg per day of L-cysteine is readily available to someone on a high protein diet. The present composition uses L-cysteine at about 50 mg/tablet or caplet, or a total of about 400 mg/day. L-cysteine bound with hydrogen chloride is naturally occurring and represents about 7.353% by weight of each tablet or caplet.

Pyridoxine

Pyridoxine, or water soluble Vitamin $B_6$, is known to be important for protein synthesis in general and may enhance glutathione production. Chaney, at pp. 976-8.

The U.S. RDA for Vitamin $B_6$ is 2 mg/day. Due to the known importance of glutathione in maintaining lens clarity, pyridoxine is added to the present composition in the dose of about 6.25 mg/tablet or caplet, or 50 mg/day. This is about 0.742% by weight of each tablet or caplet. Although the dose is much greater than the minimum daily requirement, it is apparently safe and is not an uncommon dose in multivitamins available in drugstores or grocery stores.

Riboflavin

Riboflavin, or water-soluble Vitamin $B_2$, has previously shown a good correlation with riboflavin nutritional status in older patients between those who had clear lenses and those who had cataracts. Skalka, Metabolic Ped Ophthalmol 5:17-20, 1981; Bhat, Nutr Rep Int 36:685, 1987. Glutathione reductase is necessary to reduce glutathione after oxidation, and riboflavin deficiency is associated with decreased glutathione reductase activity. Srivastava, Exp Eye Res 16:519, 1973. This enzyme is lower in cataractous lenses and would appear to be necessary if the glutathione system is to operate as an antioxidant. Beutler, Science 165:613-5, 1969; Day, Am J Ophthalmol 14:1005-9, 1931; Ono, Internat J Vit Nutr Res 46:422-6, 1976; Yagi 10th International Congress of Nutrition, Abstract No. 32-11, p. 169 (August 1975).

40 mg a day is a common dosage of riboflavin and is available in supermarkets. The U.S. RDA is about 1.7 mg. Preferably, about 7.5 mg/tablet or caplet is used in the present composition, or a total of 60 mg/day, which represents about 0.891% by weight.

The present composition may also include bioflavenoid (Vitamin P) or betacarotene (Vitamin A) as an addition to and/or substitute for one or more of the active ingredients.

As noted above, inactive elements which are well known in the art, are preferably provided as fillers to put the active elements in tablet or caplet form. For example, the fillers may include binders, lubricants, and disintigrants, which could include cellulose, gelatin, and silica.

The above active elements, considered separately, have been known to provide certain physiological effects, as described above. However, many of the studies have been animal-oriented, in vitro, and it has not been apparently known that the above combination can provide synergistic benefits. As a partial consequence thereof, whether in caplet form or otherwise, the above daily dosages can change to either a greater or smaller quantity, depending upon the severity of the disease and the patient's individual circumstances. In other words four caplets may be sufficient for one patient, while another patient may require six caplets. Eight caplets, as described above, should remain the maximum, unless special circumstances dictate otherwise. Accordingly, any treatment period can change, which is dependent upon the daily dosage. In many instances, since the objective is to prevent or slow the disease, the treatment period will be indefinite.

The above only describes preferred embodiments of the present invention, and it is contemplated that various modifications to the above can be effected but nevertheless come within the scope of the following claims.

What is claimed is:

1. A method of macular degeneration treatment, consisting essentially of the step of concurrently orally administering to a patient in need thereof an effective amount of a plurality of antioxidants for minimizing oxidative reactions;

an effective amount of a plurality of cofactors for activating metalloenzymes which react with said metalloenzymes to increase the effectiveness thereof for scavenging oxidants; and an effective amount of one or more glutathione-elevating compounds for elevating glutathione production and/or concentration;

said antioxidants including at least Vitamin E;

said cofactors being selected from the group consisting of zinc, copper, selenium, and manganese;

and said glutathione-elevating compounds being selected from the group consisting of L-cysteine or a salt thereof, pyridoxine, and riboflavin.

2. The method according to claim 1 wherein said cofactors include all of zinc, copper, selenium, and manganese.

3. The method according to claim 1 wherein the step of elevating glutathione includes the step of employing at least one of L-cysteine, pyridoxine, and riboflavin.

4. The method according to claim 1 comprising oral administration of said composition on a periodic basis each day over the course of a treatment period.

5. A method for the treatment of macular degeneration, comprising the step or orally administering to a patient in need thereof a composition consisting essentially of:

an effective antioxidant amount of a plurality of vitamins including at least Vitamins C and E;

an effective amount of a plurality of cofactors for metalloenzymes selected from the group consisting of zinc, copper, selenium, and manganese, for the activation of metalloenzymes for the scavenging of oxidants; and an effective amount of a plurality of enhancers of glutathione production and/or concentration selected from the group consisting of L-cysteine or a salt thereof, pyridoxine, and riboflavin.

6. The method according to claim 5 wherein said vitamins including glutathione-enhancing vitamins are present in an aggregate amount of at least about 39% by weight of said composition.

7. The method according to claim 5 wherein said cofactors are present in the form of a salt or bound form in an aggregate amount of at least about 2% by weight of said composition.

8. The method according to claim 5 wherein said glutathione enhancers are present in an aggregate amount of at least about 7% by weight of said composition.

9. The method according to claim 5 wherein said composition is in an orally ingestible tablet or caplet form.

10. The method according to claim 5 wherein said glutathione enhancers comprise L-cysteine or a salt thereof and riboflavin.

11. The method of claim 5 for the treatment of macular degeneration wherein said composition consists essentially of Vitamin C in an amount of at least about 29% by weight;

Vitamin E in an amount of at least about 8% by weight;

a pharmaceutically-acceptable zinc salt in an amount of at least about 1% by weight;

a pharmaceutically-acceptable copper salt in an amount of at least about 0.05% by weight;

selenium in an amount of at least about 1% by weight;

a pharmaceutically-acceptable manganese salt in an amount of at least about 0.1% by weight;

L-cystine or a pharmaceutically-acceptable salt thereof in an amount of at least about 7% by weight;

riboflavin in an amount of at least about 0.8% by weight;

all weight percentages being percentages by weight of the total composition.

12. The method of claim 11 wherein the copper salt is copper gluconate, the selenium is bound with yeast, the manganese salt is manganese gluconate, and the L-cysteine is present as such or as the hydrochloride.

13. The method of claim 11 wherein said composition also comprises pyridoxine in an amount of at least about 0.7% by weight.

* * * * *

UNITED STATES PATENT AND TRADEMARK OFFICE
CERTIFICATE OF CORRECTION

PATENT NO. : 5,075,116

DATED : Dec. 24, 1991

INVENTOR(S) : Peter G. LaHaye, Randall J. Olson

It is certified that error appears in the above-identified patent and that said Letters Patent is hereby corrected as shown below:

Column 4, line 18; "tend t glutathione" should read
  -- tend to enhance glutathione --.
Column 6, line 9; "atheroscterosis" should read
  -- atherosclerosis --.
Column 8, line 26; "32-11," should read -- 3211, --.
Column 9, line 10; "Vitamin E;" should read
  --Vitamin C and Vitamin E;--.
Column 9, line 26; "or" should read --of--.

Column 10, line 31; "weight; riboflavin" should read -- weight; and riboflavin--.

Signed and Sealed this

Thirtieth Day of March, 1993

*Attest:*

STEPHEN G. KUNIN

*Attesting Officer*     Acting Commissioner of Patents and Trademarks